United States Patent [19]
Moore et al.

[11] Patent Number: 5,827,679
[45] Date of Patent: Oct. 27, 1998

[54] CHEMICAL EVALUATION METHOD

[75] Inventors: Samuel B. Moore; Jack D. Madren, Jr.; Linda C. Ehrlich, all of Burlington; Richard A. Diehl, Greensboro, all of N.C.

[73] Assignee: Burlington Research, Inc., Burlington, N.C.

[21] Appl. No.: 823,982

[22] Filed: Mar. 25, 1997

Related U.S. Application Data

[63] Continuation of Ser. No. 418,372, Apr. 7, 1995, abandoned.
[51] Int. Cl.$^6$ ................................ C12Q 1/02; B09B 3/00
[52] U.S. Cl. ............................................ 435/29; 435/262.5
[58] Field of Search .................................. 435/29, 32, 39, 435/262, 262.5; 210/96.1, 614

[56] References Cited

U.S. PATENT DOCUMENTS 5,094,944  3/1992  Hayes ......................................... 435/29

OTHER PUBLICATIONS

Schmidt–Bleek F., Steps Toward Environmental Hazard Assessment of New Chemicals, Chemosphere 11(4) 383–415, 1982.

Vaillant M., A Multicriteria Estimation of the Environmental Risk of Chemical with the SIRIS Method, Toxicology Modeling 1(1) 57–72, 1995.

Yoshitada Y., Evaluation of the Test Method "ASRIT" Proposed by the OECD, Ecotoxicology and Environmental Safety 12 206–212, 1986.

Davis, G., Chemical Hazard Evaluation for Management Strategies: A Method for Ranking and Scoring Chemicals by Potential Human Health and Environmental Impacts, NTIS PB95–177366, Sep. 1994.

*Primary Examiner*—Ralph Gitomer
*Attorney, Agent, or Firm*—Rhodes, Coats & Bennett, L.L.P.

[57]  ABSTRACT

A method of determining the relative impact of a water soluble organic chemical comprising determining the ASRIT value of the chemical, determining the LC50 value of the chemical, determining the biodegradability value of the chemical, calculating a composite score for the chemical based upon the values determined, and comparing the composite score to comparably determined composite scores of other water soluble organic chemicals.

3 Claims, 1 Drawing Sheet

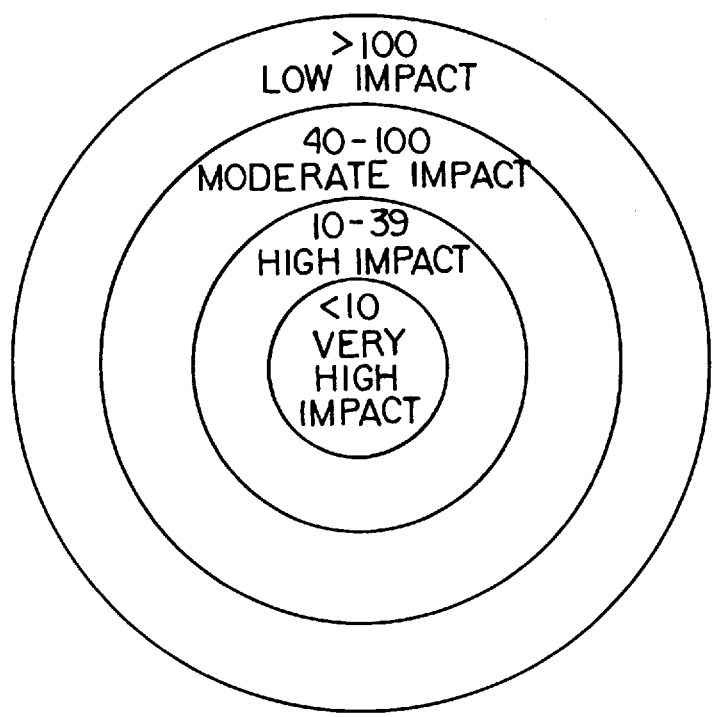

CHEMICAL EVALUATION METHOD

This application is a continuation of Ser. No. 418,372 filed Apr. 7, 1995, now abandoned.

BACKGROUND OF THE INVENTION

(1) Field of the Invention

The present invention relates generally to an improved method for evaluating the environmental impact of water soluble organic chemicals and mixtures thereof and, more particularly, to a method for comparing the relative impact of water soluble organic chemicals to aid in selecting chemicals to reduce the impact of industrial discharges.

(2) Description of the Prior Art

One way to reduce the environmental impact of aquatic discharges from industrial operations, e.g., textile manufacturing operations, is to select chemicals exhibiting lower impact relative to other chemicals available for the same purpose. Due to the complexities in evaluating the various factors contributing to the impact of a number of chemicals potentially suitable for a given purpose, however, comparison of the relative environmental impact of different chemicals is often difficult.

As used herein, the term water soluble organic chemicals is intended to include water dispersible organic chemicals. When testing or comparison of "a chemical" is described, it is to be understood that mixtures of chemicals are also contemplated.

The present invention makes this comparison possible by providing a method for developing a composite score representing the environmental impact of a given chemical based upon a plurality of values determined by individual tests of the properties of the chemical. This composite score can then be compared with comparably determined composite scores of other chemicals to determine their relative impact in order that the least environmentally impacting chemical can be chosen.

SUMMARY OF THE INVENTION

The present invention is directed to a method of determining the relative environmental impact of a water soluble organic chemicals. In making this determination, various properties of the chemical indicative of its environmental impact are evaluated. The resultant values determined by these evaluations are used to develop a composite score based upon the interrelationship of these values. This composite score can then be compared with the comparably developed composite scores of other chemicals to ascertain the impact of the chemical relative to the other chemicals.

Standardized testing procedures are employed in testing of the chemicals to permit repeatability of the tests and comparison with test results from various sources, e.g., the manufacturer of the chemical. Preferred standardized test procedures are those adopted by the Organization for Economic Cooperation & Development (OECD). The OECD tests which have been found to be especially useful in the practice of the present invention are tests used to determine the chemical's ASRIT value, its aquatic toxicity (LC50), and its biodegradability. The following description briefly summarizes these tests. The full test procedures are readily available to one skilled in the art, and are incorporated in their entirety herein by reference. It is to be understood that one practicing the invention claimed herein may determine the foregoing values through actual testing, or by reference to the results of tests conducted by others.

The Activated Sludge, Respiration Inhibition (ASRIT) Test, OECD Guideline for Testing of Chemicals 209, adopted Apr. 4, 1984, indicates the quantity of chemical which can be received by a treatment plant without impacting the viability of the biomass. The method described in this test guideline assesses the effect of a test substance on micro-organisms by measuring the respiration rate under defined conditions in the presence of different concentrations of the test substance. The method is based on that described by ETAD (Ecological and Toxicological Association of the Dyestuffs Manufacturing Industry), in which activated sludge obtained from a sewage treatment plant is used as the microbial source. The purpose of this test is to provide a rapid screening method whereby substances which may adversely affect aerobic microbial treatment plants can be identified and to indicate suitable non-inhibitory concentrations of test substances to be used in biodegradability tests. The respiration rate is the oxygen consumption of aerobic sludge or waste-water micro-organisms expressed generally as mg $O_2$ per liter per hour. EC50 is the concentration of the test substance at which the respiration rate is 50 percent of that shown by the control under conditions described in this guideline.

In the test, the respiration rate of an activated sludge fed with a standard amount of synthetic sewage feed is measured after a contact time of 30 minutes or 3 hours, or both. The respiration rate of the same activated sludge in the presence of various concentrations of the test substance under otherwise identical conditions is also measured. The inhibitory effect of the test substance at a particular concentration is expressed as a percentage of the mean respiration rates of two controls. An EC50 value is calculated from determinations at different concentrations.

The Acute Immobilization Test and Reproduction Test, OECD Guideline for Testing of Chemicals 202, Part I, adopted Apr. 4, 1984, is used to indicate the effect of untreated chemicals on fish and small crustaceans which inhabit natural freshwater systems. Effects measured include survivability and inhibition of reproduction or growth. In performing the test, Ceriodaphnia dubia or Daphnia pulex are the preferred species for testing as they are the species of daphnid most prevalently used in NPDES permit effluent acute toxicity monitoring. 24 h EC50 is the concentration estimated to immobilize 50 percent of the Daphnia after 24 hours exposure.

In the acute immobilization test a range of concentrations of the substance investigated exerts different degrees of toxic effects on the swimming capability of Daphnia under otherwise identical test conditions. Certain concentrations result in certain percentages of Daphnia being no longer capable of swimming at 24 hours. The test can be extended to 48 hours if desired. Daphnia not more than 24 hours old at the beginning of the test, laboratory bred, apparently healthy and with a known history (breeding method, pretreatment) are used in this test.

The Ready Biodegradability Test, OECD Guideline for Testing of Chemicals 301D, adopted Jul. 17, 1992, is used to determine the biodegradability of chemicals. In the test, a solution, or suspension, of the test substance in a mineral medium is inoculated and incubated under aerobic conditions in the dark or in diffuse light. Allowance is made for the endogenous impact of the inoculum by running parallel blanks with inoculum but without test substance, although the endogenous impact of cells in the presence of a chemical will not exactly match that in the endogenous control. A reference compound is run in parallel to check the operation of the procedures.

In general, degradation is followed by determining parameters such as DOC, $CO_2$ production and oxygen uptake and measurements are taken at sufficiently frequent intervals to allow the identification of the beginning and end of biodegradation. With automatic respirometers the measurement is continuous. DOC is sometimes measured in addition to another parameter but this is usually done only at the beginning and end of the test. Specific chemical analysis can also be used to assess primary degradation of the test substance and to determine the concentration of any intermediate substances formed.

Normally, the biodegradation test lasts for 28 days. Tests however may be ended before 28 days, i.e., as soon as the biodegradation curve has reached a plateau for at least three determinations. Tests may also be prolonged beyond 28 days when the curve shows that biodegradation has started but that the plateau has not been reached by day 28, but in such cases the chemical would not be classed as readily biodegradable.

In conducting the test, a solution of the chemical in mineral medium, usually at 2–5 mg/l, is inoculated with a relatively small number of micro-organisms from a mixed population and kept in completely full, closed bottles in the dark at constant temperature. Degradation is followed by analysis of dissolved oxygen over a 28 day period. The amount of oxygen taken up by the microbial population during biodegradation of chemical, corrected for uptake by the blank inoculum run in parallel, is expressed as a percentage of ThOD (theoretical oxygen demand (mg), i.e., the total amount of oxygen required to oxidize a chemical completely, expressed as mg oxygen required per mg test compound) or, less satisfactorily, COD (chemical oxygen demand (mg), i.e., the amount of oxygen consumed during oxidation of a test compound with hot, acidic dichromate, expressed as mg oxygen consumed per mg test compound).

All chemicals in all three of the foregoing tests are tested on a percent (%) actives basis, i.e., on the basis of the non-water component of the product. Product % water can be determined through application of the Karl Fisher method. If the product is not amenable to Karl Fisher, percent actives can be conducted on the basis of a total solids determination (EPA 160.3). Testing on a percent actives basis allows for standardization and also makes it possible to apply the procedure described herein to testing of mixtures.

After conducting the individual tests, a composite score for the chemical being tested is determined based upon the interrelationship of the values determined in the individual tests. When the above tests are used, this composite score is preferably calculated in accordance with the equation:

Composite Score=ASRIT Score+LC50 Score+Biodeg Score, wherein ASRIT Score=$(2.6\times(\text{ASRIT Value}^{0.4}))-1$, LC50 Score=$(4.5\times(\text{LC50 Value}^{0.5}))-(0.05\times\text{LC50 Value})$, and Biodeg Score=$(3\times(\text{Biodeg Value}^{0.775}))-2$.

The values for the multiplier and power for each of the above "Scores" are based on curve fitting empirical data on solving toxicity problems over about 15 years of research. The ranges for these scores, based on the empirical data, are shown below:

| ASRIT EC 50 | Score | Daphnia LC50 | Score | Biodegradability | Score |
|---|---|---|---|---|---|
| 0–10 mg/L | 1 | <0.1 mg/L | 1 | <20% 28 days | 1 |
| 11–250 mg/L | 5 | 0.1–1 mg/L | 5 | 20–35% 28 days | 5 |
| 251–500 mg/L | 10 | >1 ≦ 10 mg/L | 10 | 36–50% 28 days | 10 |
| 501–1000 mg/L | 20 | >10 ≦ 100 mg/L | 20 | >60% 28 days | 20 |
| >1000 mg/L | 50 | >100 mg/L | 50 | >60% 28 days | 50 |

In order to determine the relative impact of the chemical relative to other chemicals, the composite score is compared with comparably developed composite scores of other water soluble organic chemicals. One way to facilitate this comparison, is to graphically represent zones of environmental impact ranging from the very high impact to low impact, with each zone comprising a range of composite scores. For example, the zones may be graphically represented as a circular graph with a zone indicating very high impact at the center of the graph, and progressively outer annular zones indicating diminishing impact scores with the outermost zone representing low impact. The comparative scores for a plurality of chemicals can then be simply positioned on the graph to visually illustrate their relative environmental impact.

These and other aspects of the present invention will become apparent to those skilled in the art after a reading of the following description of the preferred embodiment when considered with the drawings.

BRIEF DESCRIPTION OF THE DRAWING

The FIGURE is a graph including various zones of environmental impact, each defined by the range of composite scores shown on the graph.

DESCRIPTION OF THE PREFERRED EMBODIMENTS

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

The following examples illustrate the operation of the invention.

EXAMPLE 1

Two detergents were tested according to OECD Test Procedures to determine their ASRIT values (Test No. 209), LC50 (Test No. 202), and biodegradability (Test No. 301D). Composite scores were then calculated from the values obtained by the following equation:

Composite Score=ASRIT Score+LC50 Score+Biodeg Score, wherein ASRIT Score=$(2.6\times(\text{ASRIT Value}^{0.4}))-1$, LC50 Score=$(4.5\times(\text{LC50 Value}^{0.5}))-(0.05\times\text{LC50 Value})$, and Biodeg Score=$(3\times(\text{Biodeg Value}^{0.775}))-2$.

The values obtained in the above tests, resultant composite scores, and comparable usage of these detergents in average pounds/month are shown in the following table:

TABLE 1

| Chemical | Avg Lbs/Mo | ASRIT | LC50 | Biodegradability | Score |
|---|---|---|---|---|---|
| Detergent A | 6,000 | 34 | 0.95 | 20.0 | 46-High Impact |
| Detergent B | 12,000 | 88 | 2.7 | 81.0 | 78-Moderate Impact |

EXAMPLE 2

Two nylon levelers were tested according to OECD Test Procedures to determine their ASRIT values (Test No. 209), LC50 (Test No. 202), and biodegradability (Test No. 301D). Composite scores for the two detergents were calculated from the values obtained with these tests by the equation shown in Example 1.

The values obtained in these tests, the composite scores calculated from these values, and comparable usage of the nylon levelers in average pounds/month are shown in the following table:

TABLE 2

| Chemical | Avg Lbs/Mo | ASRIT | LC50 | Biodegradability | Score |
|---|---|---|---|---|---|
| Leveler A | 3,000 | 34 | 1 | 20.0 | 47-High Impact |
| Leveler B | 10,000 | >1000 | 62 | 7.0 | 109-Moderate Impact |

Certain modifications and improvements will occur to those skilled in the art upon a reading of the foregoing description. By way of example, additional tests can be conducted and the results used in determining a composite score for a chemical, so long as comparable tests and calculations are employed for all chemicals tested, and ranges in any graph used are based on these calculations. Also, more complex calculations automatically taking into account the utilization of chemicals being compared and other relevant factors, such as dilution, can be developed based on the above calculations. It should be understood that all such modifications and improvements have been deleted herein for the sake of conciseness and readability but are properly within the scope of the follow claims.

We claim:

1. A method of determining the toxicity of a selected water soluble organic chemical relative to the toxicity of other water soluble organic alternative chemical substitutes with a combination of Organization of Economic Cooperation & Development, herein OECD, tests to aid in selecting which of the alternative chemical substitutes will reduce the impact of industrial discharges with respect to the selected chemical, comprising:

a) determining an ASRIT value based score of between 1 and 50 for said chemical by testing said chemical in accordance with OECD Activated Sludge Inhibition Test No. 209;

b) determining an $LC_{50}$ value based score of between 1 and 50 for said chemical by testing said chemical in accordance with OECD Aquatic Toxicity Test No. 202/203;

c) determining a Biodeg value based score of between 1 and 50 for said chemical by testing said chemical in accordance with OECD Biodegradability Rate Test No. 301D;

d) calculating a composite score for said chemical based upon the sum of said ASRIT, $LC_{50}$ and Biodeg scores, wherein said composite score is calculated in accordance with the equation: Composite Score=ASRIT Score+$LC_{50}$ Score+Biodeg Score, wherein ASRIT Score=$(2.6 \times (ASRIT\ Value^{0.4}))-1$, LC50 Score=$(4.5 \times (LC_{50}\ Value^{0.5}))-(0.05 \times LC_{50}\ Value)$, and Biodeg Score=$(3 \times (Biodeg\ Value^{0.775}))-2$;

e) comparing said composite score against comparably determined composite scores of other water soluble organic alternative chemical substitutes to ascertain the toxicity of the selected chemical relative to the alternate chemical substitutes to aid in selecting an alternative chemical substitute which will reduce the impact of industrial discharges with respect to the selected chemical.

2. The method of claim 1, further including making a graph comprised of a plurality of zones, with each zone representing a range of composite scores, and positioning said composite scores on said graph to visually determine their relative toxicity.

3. The method of claim 2, wherein said graph is a circular graph with a zone indicating highest toxicity at the center of said graph.

* * * * *